(12) United States Patent
Schleth et al.

(10) Patent No.: US 11,180,476 B2
(45) Date of Patent: Nov. 23, 2021

(54) HINDERED AMINE LIGHT STABILIZERS

(71) Applicant: BASF SE, Ludwigshafen (DE)

(72) Inventors: Cornelia Schleth, Grenzach-Wyhlen (DE); Liane Schulz, Freiburg i. Br. (DE); Bruno Rotzinger, Delemont (CH); Bjoern Ludolph, Ludwigshafen (DE); Manuele Vitali, Bologna (IT)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/777,303

(22) Filed: Jan. 30, 2020

(65) Prior Publication Data

US 2020/0165226 A1 May 28, 2020

Related U.S. Application Data

(63) Continuation of application No. 16/009,024, filed on Jun. 14, 2018, now abandoned, which is a continuation of application No. 15/029,970, filed as application No. PCT/EP2014/071854 on Oct. 13, 2014, now abandoned.

(30) Foreign Application Priority Data

Oct. 17, 2013 (EP) ..................................... 13189048

(51) Int. Cl.
| | | |
|---|---|---|
| *C07D 401/14* | (2006.01) | |
| *C08K 3/013* | (2018.01) | |
| *C08K 3/34* | (2006.01) | |
| *C08K 5/3492* | (2006.01) | |
| *C08K 3/04* | (2006.01) | |
| *C08K 3/22* | (2006.01) | |
| *C08K 5/00* | (2006.01) | |
| *C08K 5/132* | (2006.01) | |
| *C08K 5/134* | (2006.01) | |
| *C08K 5/524* | (2006.01) | |
| *C08K 13/02* | (2006.01) | |

(52) U.S. Cl.
CPC ............ *C07D 401/14* (2013.01); *C08K 3/013* (2018.01); *C08K 3/04* (2013.01); *C08K 3/22* (2013.01); *C08K 3/346* (2013.01); *C08K 5/005* (2013.01); *C08K 5/132* (2013.01); *C08K 5/134* (2013.01); *C08K 5/3492* (2013.01);
(Continued)

(58) Field of Classification Search
CPC .......................... C08K 5/34926; C07D 401/14
See application file for complete search history.

(56) References Cited

U.S. PATENT DOCUMENTS

| | | |
|---|---|---|
| 4,028,334 A | 6/1977 | Chalmers et al. |
| 4,108,829 A | 8/1978 | Cassandrini et al. |

(Continued)

FOREIGN PATENT DOCUMENTS

| | | |
|---|---|---|
| CA | 1 340 912 A | 2/2000 |
| CN | 103153985 A | 6/2013 |

(Continued)

OTHER PUBLICATIONS

European Search Report dated Dec. 4, 2013 in Patent Application No. 13 18 9048.

(Continued)

*Primary Examiner* — Brieann R Johnston
(74) *Attorney, Agent, or Firm* — Grüneberg and Myers PLLC

(57) ABSTRACT

A compound of formula (I)

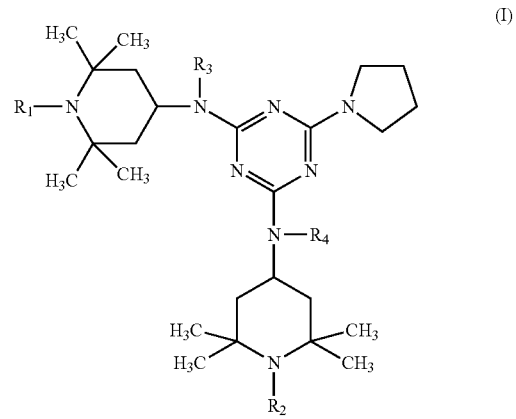

wherein
R$_1$ and R$_2$ independently of one another are hydrogen, C$_1$-C$_{22}$alkyl, —O—, —OH, —CH$_2$CN, C$_1$-C$_{18}$alkoxy, C$_2$-C$_{18}$alkoxy substituted by —OH; C$_5$-C$_{12}$cycloalkoxy, C$_3$-C$_6$alkenyl, C$_3$-C$_6$alkenyloxy, C$_7$-C$_9$phenylalkyl unsubstituted or substituted on the phenyl by 1, 2 or 3 C$_1$-C$_4$alkyl; or C$_1$-C$_8$acyl; and
R$_3$ and R$_4$ independently of one another are C$_1$-C$_{22}$alkyl or a group of the formula (Ia)

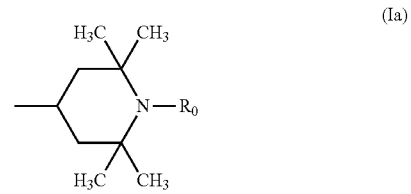

wherein R$_0$ has one of the meanings of R$_1$ and R$_2$.

18 Claims, No Drawings

(52) U.S. Cl.
CPC .......... *C08K 5/34926* (2013.01); *C08K 5/524* (2013.01); *C08K 13/02* (2013.01)

(56) References Cited

U.S. PATENT DOCUMENTS

| | | | |
|---|---|---|---|
| 4,325,863 | A | 4/1982 | Hinsken et al. |
| 4,338,244 | A | 7/1982 | Hinsken et al. |
| 4,898,688 | A * | 2/1990 | Nakahara ............ C07D 401/14 252/400.1 |
| 4,948,889 | A | 8/1990 | Cantatore et al. |
| 5,102,927 | A | 4/1992 | Rody et al. |
| 5,175,312 | A | 12/1992 | Dubs et al. |
| 5,216,052 | A | 6/1993 | Nesvadba et al. |
| 5,244,948 | A | 9/1993 | Mülhaupt et al. |
| 5,252,643 | A | 10/1993 | Nesvadba |
| 5,268,401 | A | 12/1993 | Scrima |
| 9,550,941 | B2 | 1/2017 | Menozzi et al. |
| 2012/0094565 | A1 | 4/2012 | Brunner et al. |

FOREIGN PATENT DOCUMENTS

| | | |
|---|---|---|
| DE | 38 09 628 A1 | 10/1988 |
| DE | 43 16 611 A1 | 11/1993 |
| DE | 43 16 622 A1 | 11/1993 |
| DE | 43 16 876 A1 | 11/1993 |
| EP | 0 107 615 A1 | 5/1984 |
| EP | 0 227 640 A1 | 7/1987 |
| EP | 0 291 384 A1 | 11/1988 |
| EP | 0 357 223 A2 | 3/1990 |
| EP | 0 589 839 A1 | 3/1994 |
| EP | 0 591 102 A1 | 4/1994 |
| JP | 49-21389 A | 2/1974 |
| JP | 2-53807 A | 2/1990 |

OTHER PUBLICATIONS

International Search Report dated Nov. 10, 2014 in PCT/EP2014/071854.
International Preliminary Report on Patentability and Written Opinion dated Apr. 19, 2016 in PCT/EP2014/071854.

* cited by examiner

HINDERED AMINE LIGHT STABILIZERS

CROSS REFERENCE TO RELATED APPLICATIONS

This application is a continuation application of U.S. application Ser. No. 16/009,024, filed Jun. 14, 2018, the disclosure of which is incorporated herein by reference in its entirety. U.S. application Ser. No. 16/009,024 is a continuation of U.S. application Ser. No. 15/029,970, filed Apr. 15, 2016, now abandoned, the disclosure of which is incorporated herein by reference in its entirety. U.S. Ser. No. 15/029,970 is the national stage of PCT/EP2014/071854, filed Oct. 13, 2014, the disclosure of which is incorporated herein by reference in its entirety. U.S. application Ser. No. 15/029,970 claims priority to European Application No. 13189048.5, filed Oct. 17, 2013, the disclosure of which is incorporated herein by reference in its entirety.

BACKGROUND OF THE INVENTION

The present invention relates to sterically hindered amine compounds, an organic material stabilized with the sterically hindered amine compounds against degradation induced by light, heat or oxidation, the use of the sterically hindered amine compounds as stabilizers and a method for the preparation of the sterically hindered amine compounds.

Sterically hindered amine compounds are for example described in EP-A-107615, EP-A-227640, EP-A-357223, U.S. Pat. No. 5,244,948 and U.S. Pat. No. 5,268,401.

DETAILED DESCRIPTION OF THE INVENTION

The present invention relates in particular to a compound of the formula (I)

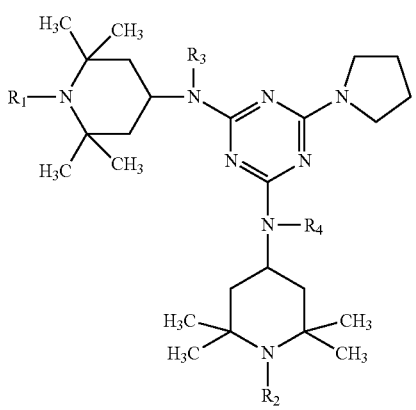

(I)

wherein
$R_1$ and $R_2$ independently of one another are hydrogen, $C_1$-$C_{22}$alkyl, —O—, —OH, —CH$_2$CN, $C_1$-$C_{18}$alkoxy, $C_2$-$C_{18}$alkoxy substituted by —OH; $C_5$-$C_{12}$cycloalkoxy, $C_3$-$C_6$alkenyl, $C_3$-$C_6$alkenyloxy, $C_7$-$C_9$phenylalkyl unsubstituted or substituted on the phenyl by 1, 2 or 3 $C_1$-$C_4$alkyl; or $C_1$-$C_8$acyl; and
$R_3$ and $R_4$ independently of one another are $C_1$-$C_{22}$alkyl or a group of the formula (Ia)

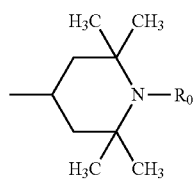

(Ia)

wherein $R_0$ has one of the meanings of $R_1$ and $R_2$.

Examples of alkyl having up to 22 carbon atoms are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetra-methylpentyl, nonyl, decyl, undecyl, 1-methylundecyl, dodecyl, 1,1,3,3,5,5-hexamethyl-hexyl, tridecyl, tetradecyl, pentadecyl, hexadecyl, heptadecyl, octadecyl and eicosyl. One preferred meaning is $C_1$-$C_4$alkyl. $R_1$ and $R_2$ are preferably methyl and $R_3$ and $R_4$ are preferably n-butyl.

Examples of alkoxy having up to 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. Preferred meanings of $R_0$, $R_1$ and $R_2$ are methoxy, ethoxy, propoxy, octoxy or undecyloxy.

Examples of $C_3$-$C_6$alkenyloxy are 1-propenyloxy and 2-propenyloxy.

An examples of $C_2$-$C_{18}$alkoxy substituted by —OH is 2-hydroxyethyl.

Examples of $C_5$-$C_{12}$cycloalkoxy are cyclopentoxy, cyclohexoxy, cycloheptoxy, cyclooctoxy, cyclodecyloxy and cyclododecyloxy. $C_5$-$C_8$Cycloalkoxy, in particular cyclopentoxy and cyclohexoxy, is preferred.

Examples of $C_7$-$C_9$phenylalkyl are benzyl and 2-phenylethyl.

$C_7$-$C_9$Phenylalkyl which is substituted on the phenyl radical by 1, 2 or 3 $C_1$-$C_4$alkyl is for example methyl benzyl, dimethylbenzyl, trimethylbenzyl or tert-butylbenzyl.

Examples of $C_3$-$C_6$alkenyl are allyl, 2-methallyl, butenyl, pentenyl and hexenyl. Allyl is preferred. The carbon atom in position 1 is preferably saturated.

Examples of $C_1$-$C_8$acyl are formyl, acetyl, propionyl, butyryl, pentanoyl, hexanoyl, heptanoyl, octanoyl, acryloyl, methacryloyl and benzoyl. $C_1$-$C_8$Alkanoyl, $C_3$-$C_8$alkenoyl and benzoyl are preferred. Acetyl and acryloyl are especially preferred.

A compound of the formula (I) wherein $R_1$ and $R_2$ independently of one another are hydrogen, $C_1$-$C_8$alkyl, $C_1$-$C_{18}$alkoxy or cyclohexyloxy and $R_3$ and $R_4$ independently of one another are $C_1$-$C_6$alkyl is preferred.

The compound of the formula (I) is preferably a compound of the formula (A).

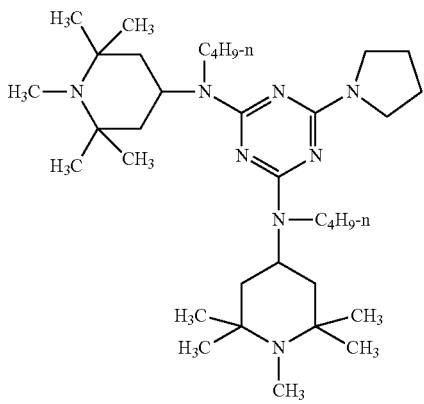

The compounds of the formula (I) can be prepared in analogy to known methods, for example by reacting a compound of the formula (II)

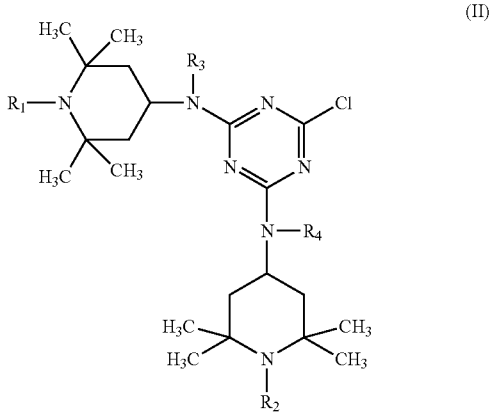

with pyrrolidine in an organic solvent, optionally in the presence of an organic or inorganic base.

According to a preferred embodiment the compound of the formula (II) is reacted with e.g. 0.8 to 5 equivalent of pyrrolidine in an organic solvent, for example toluene, xylene, chlorobenzene, nitrobenzene, mesitylene, ethylbenzene, an alcohol such as methanol, ethanol, n-propanol, i-propanol, n-butanol, t-butanol; N-methyl-2-pyrrolidone, dimethyl-formamide, 1,4-dioxane, an ester or pyrrolidine; with or without water, in the presence of e.g. 0 to 10 equivalent of an alkali metal hydroxide such as LiOH, NaOH, KOH; a carbonate or hydrogen carbonate such as $NaHCO_3$, $Na_2CO_3$, $K_2CO_3$; a solid base, a zeolite, an ion-exchange resin, an amine based base or an organic base. The concentration of the compound of the formula (II) in the organic solvent is preferably 0.1-3 molar. The reaction can be carried out e.g. under atmospheric pressure or an elevated pressure up to 60 bar. The used temperatures vary between e.g. 30° C. and 180° C. in dependence on the reaction time of e.g. 2 h to 24 h.

The starting materials of the formula (II) can be prepared in analogy to known methods, e.g. as described in U.S. Pat. No. 5,268,401.

A further embodiment of the present invention is a composition containing an organic material susceptible to degradation induced by light, heat or oxidation and a compound of the formula (I).

Examples of organic materials which can be stabilized are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly($\alpha$-methylstyrene).

6. Aromatic homopolymers and copolymers derived from vinyl aromatic monomers including styrene, $\alpha$-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or $\alpha$-methylstyrene, for example styrene on polybutadiene, styrene on polybutadiene-styrene or polybutadiene-acrylonitrile copolymers; styrene and acrylonitrile (or methacrylonitrile) on poly-butadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrite/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylensuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxybutyric acid, 4-hydroxy-valeric acid, 5-hydroxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/ MBS, PPO/HIPS, PPO/PA 6.6 and copolymers, PA/HDPE, PA/PP, PNPPO, PBT/PC/ABS or PBT/PET/PC.
30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
31. Aqueous emulsions of natural or synthetic rubber, e.g. natural latex or latices of carboxylated styrene/butadiene copolymers.

A polyolefin, an acrylonitrile/butadiene/styrene, a polyvinyl chloride, a polymethylmethacrylate, a polyamide or a polyoxymethylene are of special interest.

According to a preferred embodiment the organic material is a thermoplastic elastomer.

Examples of thermoplastic elastomers include polyolefin thermoplastic elastomers and block copolymer-type polystyrene thermoplastic elastomers. The polyolefin thermoplastic elastomers comprise polyolefin resins such as polypropylene and polyethylene serving as hard segments and rubber compositions such as ethylene-propylene-diene-elastomer (EPDM) serving as soft segments. The block copolymer-type polystyrene thermoplastic elastomer comprises polystyrene serving as hard segments and polydienes such as polybutadiene or polyisoprene serving as soft segments.

Alternatively, a blend of the polyolefin elastomers and the polystyrene elastomers may also be used as the thermoplastic elastomer of the present invention. The methods for combining soft segments and hard segments in thermoplastic elastomers may be roughly divided into simple blending, implantation by copolymerization, and dynamic cross-linking. Combinations of segments of polystyrene thermoplastic elastomers include a styrene-butadiene-styrene block copolymer (SBS), a styrene-isoprene-styrene block copolymer (SIS), a styrene-ethylene butylene-styrene block copolymer (SEBS), a styrene-ethylene propylene-styrene block copolymer (SEPS), a hydrogenated polymer of any one of the four copolymers, a hydrogenated polymer of random SBR (HSBR), and a blend of polypropylene and one or more arbitrary members selected from among these polymers. (SBR=styrene butadiene rubber)

Of interest is a thermoplastic polyolefin, in particular polyethylene or polypropylene containing a rubber phase based on ethylene and/or propylene.

The compounds of the formula (I) can be used in various proportions depending on the nature of the organic material to be stabilized, on the end use and on the presence of other additives.

In general, it is appropriate to use, for example, 0.01 to 5% by weight of a compound of the formula (I), relative to the weight of the organic material, preferably 0.05 to 2%, in particular 0.05 to 1%.

The compounds of the formula (I) can be added, for example, to polymeric materials before, during or after the polymerization or crosslinking of the said materials. Furthermore, they can be incorporated in the polymeric materials in the pure form or encapsulated in waxes, oils or polymers.

In general, the compounds of the formula (I) can be incorporated in the organic materials by various processes, such as dry mixing in the form of powder, or wet mixing in the form of solutions or suspensions or also in the form of a masterbatch which contains the compounds of the formula (I) in a concentration of 2.5 to 25% by weight; in such operations, the polymer can be used in the form of powder, granules, solutions, suspensions or in the form of latices.

Examples of processing of the compositions according to the present invention are: Injection blow molding, extrusion, blow molding, rotomolding, in mold decoration (back injection), slush molding, injection molding, co-injection molding, forming, compression molding, pressing, film extrusion (cast film; blown film), fiber spinning (woven, non-woven), drawing (uniaxial, biaxial), annealing, deep drawing, calandering, mechanical transformation, sintering, coextrusion, coating, lamination, crosslinking (radiation, peroxide, silane), vapor deposition, weld together, glue, vulcanization, thermoforming, pipe extrusion, profile extrusion, sheet extrusion; sheet casting, spin coating, strapping, foaming, recycling/rework, extrusion coating, visbreaking (peroxide, thermal), fiber melt blown, spun bonded, surface treatment (corona discharge, flame, plasma), sterilization (by gamma rays, electron beams), gel-coating, tape extrusion, SMC-process or plastisol.

The compositions according to the present invention can be advantageously used for the preparation of various shaped articles. Examples are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded plates, glazing for buildings (monolithic, twin or multiwall), aircraft, schools, extruded sheets, window film for architectural glazing, train, transportation and sanitary articles.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V-1) Films (packaging, dump, laminating, bale wrap, swimming pools, waste bags, wallpaper, stretch film, raffia, desalination film, batteries, and connectors.

V-2) Agricultural films (greenhouse covers, tunnel, mulch, silage, bale wrap), especially in presence of intensive application of agrochemicals.

VI-1) Food packing and wrapping (flexible and solid), BOPP, BOPET, bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

An automotive interior or exterior trim material made of a composition according to the present invention is preferred. Particularly preferred shaped articles are those listed above under I-2. Of interest is also a facing material for a roof, seat or dashboard.

If desired, one or more conventional additives for synthetic polymers, such as antioxidants, UV absorbers, nickel stabilizers, pigments, fillers, plasticizers, corrosion inhibitors and metal deactivators, can be added to the organic materials containing the compounds of the formula (I).

Examples of conventional additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butyl hydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy2-methylphenyl)-4-n-dodecylmercaptobutane, 1,1,5,5-tetra-(5-tert-butyl-4-hydroxy-2methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis (3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4- tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenyl propionyl)-hexahydro-1,3,5-triazine, 1,3,5-tris(3,5-dicyclohexyl-4-hydroxybenzyρisocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethyl hexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl) amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenyl methane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3', 5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl) benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

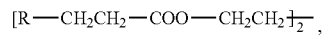

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethyl butyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate).

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butyl benzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example carbonic acid bis(1-undecyloxy-2,2,6,6-tetramethyl-4-piperidyl)ester, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyhexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine,

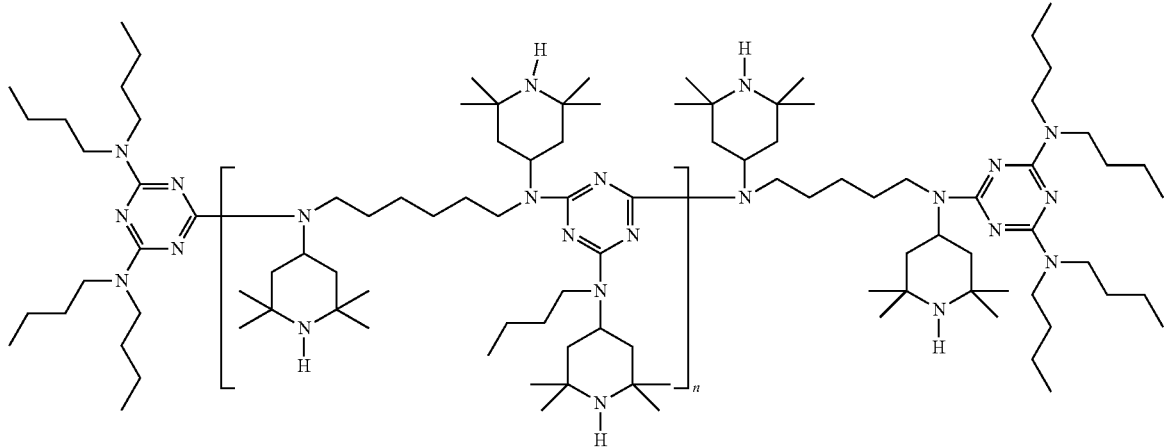

(Chimassorb ® 2020)

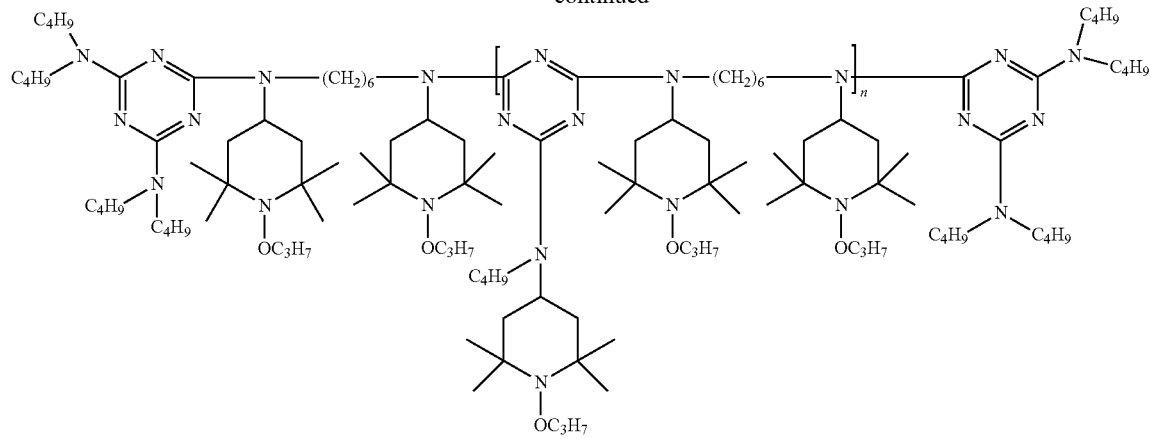

(Tinuvin® NOR 371)

2.7. Oxamides, for example 4,4'-dioctyloxyoxanilide, 2,2'-diethoxyoxanilide, 2,2'dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethyl phenyl)-1,3,5-triazine, 2,4-bis(4-[2-ethylhexyloxy]-2-hydroxyphenyl)-6-(4-methoxyphenyl)-1,3,5-triazine, 2-(4,6-bis-biphenyl-4-yl-1,3,5-triazin-2-yl)-5-(2-ethyl-(n)-hexyloxy)phenol.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxy-pentaerythritol diphosphite, bis(2,4-di-tert-butyl-6-methylphenyl)pentaerythritol diphosphite, bis(2,4,6-tris(tert-butyl phenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'biphenyl-2,2'diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butyl phenoxy)-1,3,2-dioxaphosphirane.

The following phosphites are especially preferred:
Tris(2,4-di-tert-butylphenyl) phosphite (Irgafos®168, Ciba Specialty Chemicals Inc.), tris(nonylphenyl) phosphite,

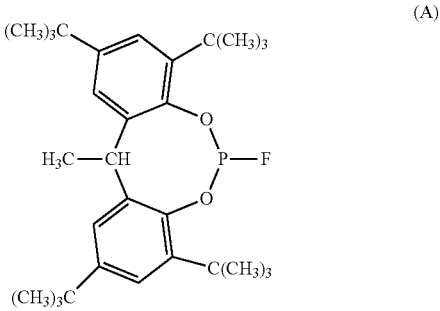

(A)

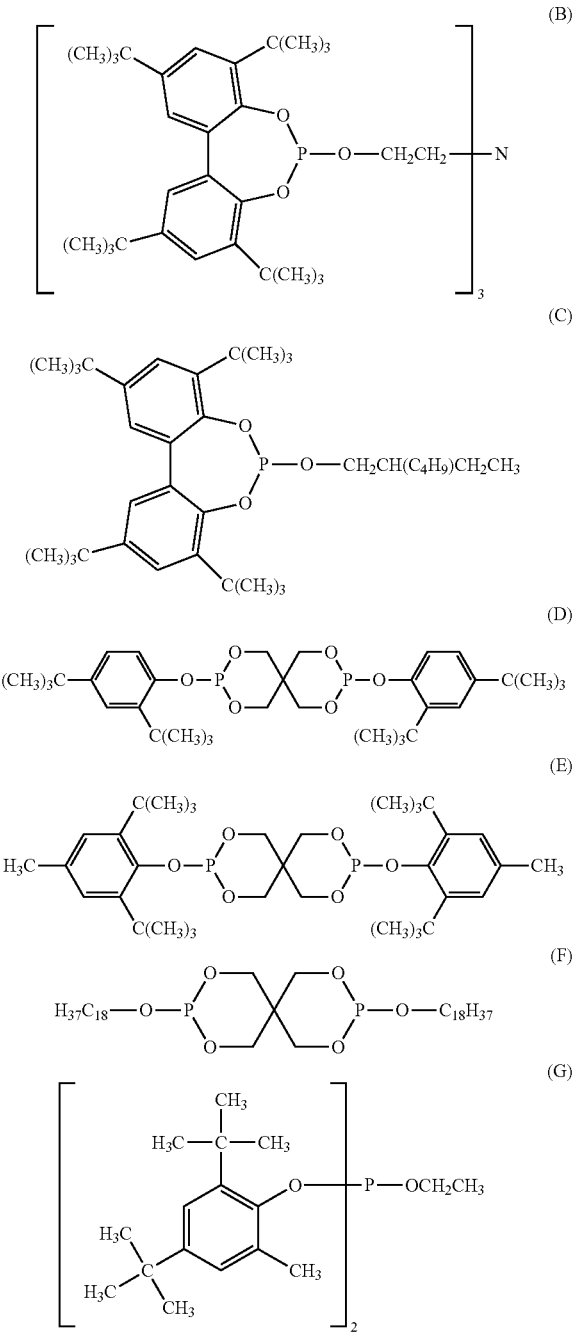

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate, pentaerythritol tetrakis[3-(dodecylthio)propionate] or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, Wallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di (benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, anti-static agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butyl benzofuran-2-one, 3-(2,3-dimethylphenyl)-5,7-di-tert-butylbenzofuran-2-one, 3-(2-acetyl-5-isooctylphenyl)-5-isooctylbenzofuran-2-one.

Phenolic antioxidants are preferred. Of interest are those listed above under item 1. Of particular interest are phenolic antioxidants and process stabilizers such as pentaerythritol tetrakis[3,5-di-tert-butyl-4-hydroxyphenylpropionate], octadecyl-3-(3,5-di-tert-butyl-4-hydroxyphenyl)proprionate, 1,3,5-tris(3,5-di-tert-butyl-4-hydroxybenzyl)-2,4,6-trimethylbenzene, N,N'-bis(3,5-di-tert-butyl-4-hydroxyphenylpropionyl)hexamethylene-diamide, 1,3,5-tris[3,5-di-tert-butyl- 4-hydroxybenzyl]isocyanurate, 2,4-di-t-butylphenyl-3,5-di-t-butyl-4-hydroxybenzoate, bis(1,2,2,6,6-pentamethylpiperidin-4-yl)-butyl(3,5-di-t-butyl-4-hydroxybenzyl)malonate) and tris[2,4-di-tert-butylphenyl]phosphite.

Further preferred additives are pentaerythritol tetrakis[3-(dodecylthio)propionate] and Ca stearate.

Pigments such as $TiO_2$ and carbon black are further preferred. Fillers such as talc are also of interest.

Preferred additives are also sterically hindered amine light stabilizers and/or UV-absorbers, in particular those listed above under item 2.

The weight ratio of the compound of the formula (I) to the conventional additive is for example 1:100 to 100:1, preferably 1:100 to 10:1, in particular 1:10 to 10:1.

Another object of the present invention is method for stabilizing an organic material against degradation induced by light, heat or oxidation which comprises incorporating into said organic material at least one compound of the formula (I).

The examples below illustrate the invention in greater detail. All percentages and parts mentioned in the present application are by weight, unless stated otherwise.

EXAMPLE 1

Preparation of 2N,4N'-dibutyl-2N,4N'-bis(1,2,2,6,6-pentamethyl-4-piperidyl)-6-pyrrolidin-1-yl-1,3,5-triazine-2,4-diamine (=Compound A)

The starting material 2N,4N'-dibutyl-6-chloro-2N,4N'-bis(1,2,2,6,6-tetramethylpiperidin-4-yl)-1,3,5-triazine-2,4-diamine is known and can be prepared in analogy to known methods, e.g. as described in Example 2A of U.S. Pat. No. 5,268,401.

Method A:

43.19 g of 2N,4N'-dibutyl-6-chloro-2N,4N'-bis(1,2,2,6,6-tetramethylpiperidin-4-yl)-1,3,5-triazine-2,4-diamine, 5.6 g of pyrrolidine, 15 g of aqueous sodium hydroxide (30%) and 30 g of xylene are added in a steel autoclave. The reactor is three times flashed with argon. Then, the reactor is heated up to 160° C. for 20 h. After complete conversion, the reaction mixture is diluted with water and toluene, the phases are separated and the organic layer is washed with water several times. After drying over sodium sulfate 51.1 g of white cured solid is obtained. The product is solved in 150 ml of hot hexane and the crystals are filtered off and dried. As yield, 41.6 g of white product (=89% of theory) are isolated.

TLC (n-hexane/ethyl acetate 2:1 plus 5 drops ammonium hydroxid solution): Rf=0.82.

1H NMR: (400 MHz, CHLOROFORM-d): ppm 5.17 (2H, m), 3.49 (4H, dd), 3.33 (4H, dd), 2.25 (6H, s), 1.87 (4H, dd), 1.67-1.50 (12H, m), 1.37-1.22 (4H, m), 1.16 (12H, s), 1.10 (12H, s), 0.96-0.86 (6H, m).

Method B:

93.4 g of 2N,4N'-dibutyl-6-chloro-2N,4N'-bis(1,2,2,6,6-tetramethylpiperidin-4-yl)-1,3,5-triazine-2,4-diamine are dissolved in 86.5 ml of xylene. 12.0 g of pyrrolidine, 23.2 g of aqueous sodium hydroxide (30%) and 29.9 g of water are added and the solution is heated up to 70° C. for 3 h. After complete reaction the phases are split and the organic phase is washed with water several times. Solvent is removed at 200° C., 50 mbar. The hot melt is filled on a plate and cooled down. The product (90.0 g (=90% of theory) is a yellow brownish melt with a solidification temperature of 75-80° C.

Form Giving:

The obtained solidified product can be converted into a highly crystalline product form on an extrusion after seeding with crystalline material.

Melting point: 165-172° C.

EXAMPLE 2

Stabilization of a Thermoplastic Polypropylene

Base Formulation:

79.275% by weight of thermoplastic polypropylene (Daplen® EE013 AE of Borealis;

Melt Flow Rate: 11 g/10 min (ISO 1133); Density: 905 kg/m$^3$ (ISO 1183)

20% by weight of talc, 0.225% by weight of carbon, and 0.5% by weight of $TiO_2$.

Preparation of the Tested Specimen:

The base formulation is pre-mixed in a Pappermaier® ESK-150 mixer. This mixture is combined with 0.2% by weight of Compound (A) on a Mixaco Lab CM12 high speed mixer and then compounded on a Berstorff® ZE 25×32 D extruder at 220° C. The full formulation is then injection molded on an Engel H L65 injection molding machine at 240° C.

The injection molded plaques 40 mm×60 mm×2 mm or 25 mm×60 mm×2 mm are exposed to artificial weathering according to the international norm SAE J2412. The parameters measured are color deviation (Delta E) and gloss at 60°.

The results are listed in Tables 1 and 2.

TABLE 1

| Delta E (Low values are desired.) | | | | | | | |
|---|---|---|---|---|---|---|---|
| Sterically hindered | Hours exposure | | | | | | |
| amine | 0 | 500 | 990 | 1490 | 1990 | 2510 | 2930 | 3110 |
| None | 0 | 13.5 | 15.2 | — | — | — | — | — |
| Compound A | 0 | 0.2 | 0.9 | 1.3 | 1.3 | 1.7 | 1.3 | 1.5 |

TABLE 2

| Gloss at 60° (High values are desired.) | | | | |
|---|---|---|---|---|
| Sterically hindered | Hours exposure | | | |
| amine | 0 | 1990 | 2510 | 3000 |
| None | 21.5 | — | — | — |
| Compound A | 22.3 | 25.8 | 26.5 | 26.5 |

EXAMPLE 3

Stabilization of a Thermoplastic Polypropylene

The test specimens are prepared in analogy to the method described in Example 2 and are evaluated for their stickiness according to VW PV1306 standard after artificial weathering.

Evaluation Parameters:

|  | Rating |
| --- | --- |
| Sample ok | 1 |
| lackluster/but NOT sticky | S |
| Slightly sticky | 2 |
| Sticky | 3 |
| Very sticky | 4 |
| Resinified | H |
| Wax-like | W |
| Test terminated, microcracks | X |

*) The rating is the result of the evaluation of 3-5 people.

TABLE 3

| | Stickiness | | | | |
| --- | --- | --- | --- | --- | --- |
| Sterically hindered | Rating after | | | | |
| amine | 0 | 3 cycles | 9 cycles | 13 cycles | 18 cycles |
| None | 1 | 1 | 1 | 1-S | Sample is destroyed |
| 0.2% of Compound A | 1 | 1 | 1 | 1 | 1 |

A cycle corresponds to 96 hours.

The results shown above clearly reveal that Compound A does not add further stickiness to the thermoplastic polypropylene samples.

EXAMPLE 4

Stabilization of a Thermoplastic Acrylonitrile/Butadiene/Styrene (ABS)

The following two formulations are prepared based on ABS (Styrolution Terluran®GP-22, which is an easy-flow, general purpose injection molding grade with high resistance to impact and heat distortion, intended for a wide range of applications, with 19 cm³/10 min Melt Volume Rate, 220° C./10 kg):

"Standard Polymer":

96.00% of Terluran®GP-22

3.00% of Titanium Dioxide Kronos®2220

1.00% of Acrawax®C Powder

Formulation No 1:

100.00% "of Standard Polymer"

Formulation No 2:

99.65% of "Standard Polymer"

0.25% of Compound A 0.10% of Paraffin Oil

Preparation of the Tested Specimen:

The formulations are pre-mixed in a Röhnrad Elite 650 mixer and then compounded on a Berstorff® ZE 25×32 D extruder at 220° C. After compounding the formulations are dried for 2 hours at 80° C. and then injection molded on an Arburg 320 S injection molding machine at 240° C.

The injection molded plaques with sizes of 68 mm×44 mm×2 mm are exposed to artificial weathering according to the international norm ASTM G 155-C1. The parameters measured are color deviation (Delta E, aperture 20 mm, D65, 10°). The results are listed in Table 4.

TABLE 4

| | Delta E*) after weathering time according to ASTM G 155-C1 in h | | | |
| --- | --- | --- | --- | --- |
| Formulation | 0 | 168 | 336 | 672 |
| No. 1 | 0.0 | 0.3 | 3.7 | 12.0 |
| No. 2 | 0.0 | 0.8 | 1.8 | 8.2 |

*) Low values are desired.

EXAMPLE 5

Stabilization of a Thermoplastic Flexible Polyvinyl Chloride (PVC)

"Standard Polymer":

64.73% of Norvinyl®S7060 (Vinyl chloride homopolymer)

32.36% of Palatinol®N (Plasticiser)

1.61% of Drapex®39 (Epoxidised soy bean oil)

1.30% of Baerostab®CT 9051 XRF (CaZn Stabilizer)

Formulation No. 1:

100.00% of "Standard polymer"

Formulation No. 2:

99.50% of "Standard polymer"

0.25% of Chimassorb®81 (2-hydroxy-4-octyloxy-benzophenone)

0.25% of Compound A

Preparation of the Tested Specimen:

The formulations are pre-mixed per tumble mixer and then compounded for 7 min on a Collin® two-roll-mill at 160° C. with 0.4 mm gap. The films obtained are then exposed to artificial weathering according to the international norm ASTM G 154-C1. The parameter measured is color deviation (Delta E, aperture 20 mm, D65, 10°). The results are listed in Tables 5.

TABLE 5

| | Delta E*) after weathering time according to ASTM G 154-C1 in h | |
| --- | --- | --- |
| Formulation | 0 | 250 |
| No. 1 | 0 | 0.35 |
| No. 2 | 0 | 0.18 |

*) Low values are desired.

EXAMPLE 6

Stabilization of a Polymethylmethacrylate (PMMA) Solution Cast Film (1)

10 g of Plexiglas 7 N (Evonik) are dissolved in 40 g of methylene chloride together with 50 mg of Compound A. Films are drawn with the help of an automatic blade (Erichsen®) with a blade speed of 12 mm/sec and a gap height of 120 μm. The films are then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table 6.

TABLE 6

|  | hours | | | | | | | | |
| --- | --- | --- | --- | --- | --- | --- | --- | --- | --- |
|  | 0 | 99 | 263 | 472 | 1006 | 1504 | 2017 | 2498 | 2998 | 3987 |
| YI (Yellowness Index)*) | 0.1 | 0.4 | 0.3 | 0.4 | 0.6 | 0.3 | 0.7 | 0.5 | 0.5 | 0.8 |
| ΔE (Color difference)*) | 0.0 | 0.3 | 0.1 | 0.3 | 0.5 | 0.3 | 0.5 | 0.3 | 0.3 | 0.5 |
| b* (Color coordinate)*) | 0.2 | 0.4 | 0.3 | 0.3 | 0.4 | 0.3 | 0.5 | 0.4 | 0.4 | 0.5 |

*)Low values are desired.

EXAMPLE 7

Stabilization of a Polymethylmethacrylate (PMMA) Solution Cast Film (2)

10 g of Plexiglas 7 N (Evonik) are dissolved in 40 g of methylene chloride together with 50 mg of Compound A and 100 mg of 2,2'-methylenebis(6-(2H-benzotriazol-2-yl)-4-1,1,3,3-tetramethylbutyl)phenol (Tinuvin®360). Films are drawn with the help of an automatic blade (Erichsen®) with a blade speed of 12 mm/sec and a gap height of 120 μm. The freshly drawn film is dried for 10 minutes. The resulting film with a thickness of 25 μm has a yellowness index of 16.3. (DIN 6167(1980-01)). This film is then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table 7.

TABLE 7

|  | hours | | | | | | | | |
| --- | --- | --- | --- | --- | --- | --- | --- | --- | --- |
|  | 0 | 99 | 263 | 472 | 1006 | 1504 | 2017 | 2498 | 2998 | 3987 |
| YI (Yellowness Index)*) | 0.0 | 0.6 | 0.2 | 0.7 | 1.1 | 1.0 | 1.4 | 1.1 | 1.3 | 1.6 |
| ΔE (Color difference)*) | 0.0 | 0.6 | 0.2 | 0.6 | 0.9 | 0.7 | 1.0 | 0.7 | 0.8 | 1.0 |
| b* (Color coordinate)*) | 0.1 | 0.5 | 0.3 | 0.5 | 0.8 | 0.7 | 0.9 | 0.8 | 0.8 | 1.0 |

*)Low values are desired.

EXAMPLE 8

Stabilization of a Polymethylmethacrylate (PMMA) Cast Thick Sheet (1)

70 g of freshly distilled methylmethacrylate are mixed with 70 mg of lauroylperoxide and 105 mg of Compound A. The mixture is degassed and heated in a twist-off glass for 3 hours in a waterbath at 60° C. The prepolymerized syrup is poured between two glass plates, with 1.8 mm distance, which are sealed on three sides. This glass sandwich is kept for 16 hours at 60° C. in an oven, followed by 3 hours at 120° C. The resulting polymethylmethacrylate (PMMA) sheet has a yellowness index of 32.2 (DIN 6167 (1980-01)). This sheet is then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table 8.

TABLE 8

|  | hours | | | | | | | | | |
| --- | --- | --- | --- | --- | --- | --- | --- | --- | --- | --- |
|  | 0 | 255 | 496 | 733 | 999 | 1502 | 2005 | 2494 | 3028 | 4035 | 4995 |
| YI (Yellowness Index)*) | 2.7 | 1.2 | 0.7 | 0.3 | 0.3 | 0.3 | 0.2 | 0.2 | 0.2 | 0.2 | 0.4 |
| ΔE (Color difference)*) | 0.0 | 1.3 | 1.6 | 1.8 | 1.9 | 1.9 | 1.9 | 1.9 | 1.9 | 1.9 | 1.9 |
| b* (Color coordinate)*) | 2.0 | 0.8 | 0.6 | 0.3 | 0.3 | 0.3 | 0.2 | 0.2 | 0.3 | 0.3 | 0.3 |

*)Low values are desired.

EXAMPLE 9

Stabilization of a Polymethylmethacrylate (PMMA) Thick Sheet (2)

70 g of freshly distilled methylmethacrylate are mixed with 70 mg of lauroylperoxide, 105 mg of Compound A and 105 mg of 2-(2H-benzotriazol-2-yl)-p-cresol (Tinuvin®P). The mixture is degassed and heated in a twist-off glass for 3 hours in a waterbath at 60° C. The prepolymerized syrup is poured between two glass plates, with 1.8 mm distance, which are sealed on three sides. This glass sandwich is kept for 16 hours at 60° C. in an oven, followed by 3 hours at 120° C. The resulting PM MA sheet has a yellowness index of 32.2 (DIN 6167 (1980-01)). This sheet is then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table 9.

TABLE 9

| | hours | | | | | | | | | | |
|---|---|---|---|---|---|---|---|---|---|---|---|
| | 0 | 255 | 496 | 733 | 999 | 1502 | 2005 | 2494 | 3028 | 4035 | 4995 |
| YI (Yellowness Index)*) | 3.1 | 0.5 | 0.5 | 0.5 | 0.6 | 0.7 | 0.6 | 0.7 | 0.7 | 0.8 | 1.0 |
| ΔE (Color difference)*) | 0.0 | 1.9 | 1.9 | 1.9 | 1.9 | 1.8 | 1.8 | 1.8 | 1.8 | 1.8 | 1.7 |
| b* (Color coordinate)*) | 2.2 | 0.5 | 0.4 | 0.4 | 0.5 | 0.5 | 0.5 | 0.6 | 0.6 | 0.6 | 0.7 |

*)Low values are desired.

EXAMPLE 10

Stabilization of Polyamide PA6 (1)

4000 g of PA6 (Ultramid®B40, BASF) is cryo-ground and dried in a vacuum oven at 80° C. for 4 hours. In a MTI M20 FU high-speed mixer the ground polymer is mixed with 12 g of Irganox®B 1171 (Blend of 50% of tris(2,4-di-tert-butylphenyl)phosphite and 50% of N,N'-hexane-1,6-diyl-bis[3-(3,5-di-tert-butyl-4-hydroxyphenyl)propionamide)]) and 10 g of Compound A. The powder mixture is then compounded on a Berstorff®ZE 25×32 D at 250° C. and after drying in a Heliomat 2000 6K drier extruded on a Collin®CR-136/350 film extrusion line to 50 µm thick films.

These films are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). Color is measured in accordance to DIN 6167 (1980-01). The results are listed in Table 10.

TABLE 10

| | hours | | | | | |
|---|---|---|---|---|---|---|
| | 0 | 100 | 248 | 500 | 737 | 994 |
| YI (Yellowness Index)*) | 0.1 | 0.3 | 0.4 | 0.5 | 0.6 | 0.8 |
| b* (Color coordinate)*) | 0.2 | 0.3 | 0.4 | 0.4 | 0.4 | 0.5 |

*)Low values are desired.

EXAMPLE 11

Stabilization of Polyamide PA6 (2)

4000 g of PA6 (Ultramid®B40, BASF) is cryo-ground and dried in a vacuum oven at 80° C. for 4 hours. In a MTI M20 FU high-speed mixer the ground polymer is mixed with 12 g of lrganox®B 1171 (Blend of 50% of tris(2,4-di-tert-butylphenyl)phosphite and 50% of N,N'-hexane-1,6-diyl-bis[3-(3,5-di-tert-butyl-4-hydroxyphenyl)propionamide)]) and 20 g of Compound A. The powder mixture is then compounded on a Berstorff®ZE 25×32 D at 250° C. and after drying in a Heliomat 2000 6K drier extruded on a Collin®CR-136/350 film extrusion line to 50 µm thick films.

These films are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). Color is measured in accordance to DIN 6167 (1980-01). The results are listed in Table 11.

TABLE 11

| | hours | | | | | |
|---|---|---|---|---|---|---|
| | 0 | 100 | 248 | 500 | 737 | 994 |
| YI (Yellowness Index)*) | 0.1 | 0.4 | 0.3 | 0.4 | 0.3 | 0.6 |
| b* (Color coordinate)*) | 0.2 | 0.3 | 0.3 | 0.3 | 0.3 | 0.4 |

*)Low values are desired.

EXAMPLE 12

Stabilization of Polyoxymethylene (POM) (1)

2500 g of POM (Ultraform®N2320 003, BASF) is cryo-ground and dried in a vacuum oven at 80° C. for 4 hours. In a Mixaco®Lab CM 12 high-speed mixer the ground polymer is mixed with 7.5 g of Compound A and 3.75 g of ethylene bis(oxyethylene) bis-(3-(5-tert-butyl-4-hydroxy-m-tolyl)-propionate) (Irganox®245). The powder mixture is then compounded on a Berstorff®ZE 25×32 D at 190° C. and after drying in a Heliomat 2000 6K drier injection molded to 2 mm thick plaques on a Engel HL 65 at 190° C.

These plaques are exposed to xenon light in accordance to ASTM G 155 Cycle 1 (Xe light, 2 borosilicate filters "S", 0.35 W/m2 at 340 nm, 63° C.±3 ° C., 50-60% rel. humidity, continuous light, 102 minutes dry followed by 18 minutes water spray). Color is measured in accordance to DIN 6167 (1980-01). The results are listed in Table 12.

TABLE 12

| hours | 0 | 98 | 262 | 499 | 776 |
|---|---|---|---|---|---|
| YI (Yellowness Index)*) | 4.4 | 1.9 | 3.0 | 3.5 | 4.1 |
| b* (Color coordinate)*) | 2.7 | 1.3 | 1.9 | 2.2 | 2.5 |

*)Low values are desired.

EXAMPLE 13

Stabilization of Polyoxymethylene (POM) (2)

2500 g of POM (Ultraform®N2320 003, BASF) is cryo-ground and dried in a vacuum oven at 80° C. for 4 hours. In a Mixaco®Lab CM 12 high-speed mixer the ground polymer is mixed with 7.5 g of Compound A, 3.75 g of ethylene bis(oxyethylene) bis-(3-(5-tert-butyl-4-hydroxy-m-tolyl)-propionate) (Irganox®245) and 7.5 g of 2-(2H-benzotriazol-2-yl)-4,6-bis(1-methyl-1-phenylethyl)phenol (Tinuvin® 234). The powder mixture is then compounded on a Berstorff®ZE 25×32 D at 190° C. and after drying in a Heliomat 2000 6K drier injection molded to 2 mm thick plaques on a Engel HL 65 at 190° C.

These plaques are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). Color is measured in accordance to DIN 6167 (1980-01). The results are listed in Table 13.

TABLE 13

| hours | 0 | 98 | 262 | 499 | 776 |
|---|---|---|---|---|---|
| YI (Yellowness Index)*) | 7.0 | 4.1 | 4.4 | 4.4 | 4.6 |
| b* (Color coordinate)*) | 4.2 | 2.7 | 2.8 | 2.8 | 2.9 |

*)Low values are desired.

EXAMPLE 14

Stabilization of an Agricultural Low Density Polyethylene (LDPE) Film

LDPE films for agricultural application are prepared as follows: 100 g of the light stabilizer listed in Tables 14-1 and 14-2, 5 g of Irganox®B900 (80% of tris(2,4-di-tert-butylphenyl)phosphite and 20% of octadecyl-3-(3,5-di-tert-butyl-4-hydroxyphenyl)-propionate) as process stabilizer and 895 g of polyethylene powder (Versalis Riblene®FF 29, characterized by a density of 0.921 g/cm$^3$ and a melt flow index (190° C./2.16 Kg) of 0.6 g/10') are mixed in a turbo-mixer. The masterbatch formulation is extruded at a maximum temperature of 200° C. in a lab-scale OMC twin-screw extruder (Ø19 mm, L/D=25). A defined aliquot of the granules so obtained are mixed with 50 g of a polyethylene masterbatch containing 5% of Irganox®B900 as process stabilizer and with an amount of the above described virgin polyethylene in pellets to get a 10000 g formulation, in a Rhonrad slow mixer for 10 minutes, resulting in the final formulation that contains 0.6% in total of light stabilizer. Finally this formulation is blown in a semi-industrial Dolci®blow-extruder (Ø40 mm, L/D=26) at a maximum temperature of 210° C. to give a 150 μm thick film.

Artificial Weathering:

Film specimens from the formulation prepared as described above are cut and exposed in the Weather-o-Meter (WOM, as per ASTM G155, dry cycle), for accelerated light weathering. Specimens are taken at defined intervals of time after exposure and underwent tensile testing: the residual elongation at break is measured, by means of a constant velocity tensiometer (as per ISO 527), in order to evaluate the decay of the mechanical properties of the plastic film, as a consequence of the polymer degradation. The results of the evaluations are listed in Table 14-1:

TABLE 14-1

| Light Stabilizer | Time (hours) to 50% of the initial elongation |
|---|---|
| 0.6% of Compound A | 5075 |

The above table shows an excellent light stabilization effect of Compound A.

Artificial Weathering Combined with Chemical Treatment (Sulfurous Acid):

Film specimens prepared as described above are cut and dipped into a 0.1 N solution of sulfurous acid for 24 hours. This simulates the effect of an acidic environment caused by many agrochemicals.

After letting the film specimens dry under a fume hood, the treated films are exposed in the Weather-o-Meter (WOM, as per ASTM G155, dry cycle), for accelerated light weathering. Specimens of the formulations are taken at defined intervals of time after exposure and underwent tensile testing, as described above. The results of the evaluations are listed in Table 14-2.

TABLE 14-2

| Light Stabilizer | Time (hours) to 50% of the initial elongation |
|---|---|
| 0.6% of Compound A | 4040 |

The above table shows an excellent light stabilization effect of Compound A in the presence of agrochemicals.

The invention claimed is:

1. A compound of formula (I)

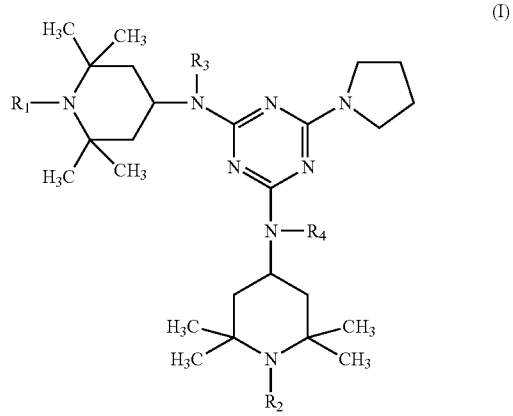

wherein $R_1$ and $R_2$ independently of one another are hydrogen, $C_1$-$C_{22}$alkyl, —O, —OH, —CH$_2$CN, $C_1$-$C_{18}$alkoxy, $C_2$-$C_{18}$alkoxy substituted by —OH, $C_5$-$C_{12}$cycloalkoxy, $C_3$-$C_6$alkenyl, $C_3$-$C_6$alkenyloxy, $C_7$-$C_9$phenylalkyl unsubstituted or substituted on the phenyl by 1, 2 or 3 $C_1$-$C_4$alkyl; or $C_1$-$C_8$acyl; and $R_3$ and $R_4$ independently of one another are a group of formula (Ia)

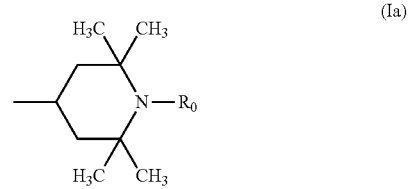

wherein $R_0$ has one of the meanings of $R_1$ and $R_2$.

2. The compound according to claim 1, wherein $R_1$ and $R_2$ independently of one another are hydrogen, $C_1$-$C_8$alkyl, $C_1$-$C_{18}$alkoxy or cyclohexyloxy.

3. A composition comprising:

an organic material susceptible to degradation induced by light, heat or oxidation, and the compound according to claim 1.

4. The composition according to claim 3, wherein the organic material is a thermoplastic polymer.

5. The composition according to claim 3, wherein the organic material is a polyolefin, an acrylonitrile/butadiene/styrene, a polyvinyl chloride, a polymethylmethacrylate, a polyamide or a polyoxymethylene.

6. The composition according to claim 3, wherein the organic material is a thermoplastic polyolefin.

7. The composition according to claim 3, wherein the organic material is a thermoplastic polyethylene or polypropylene.

8. The composition according to claim 3, further comprising a phenolic antioxidant and/or a phenolic phosphite.

9. The composition according to claim 8, wherein the phenolic antioxidant is pentaerythritol tetrakis[3,5-di-tert-butyl-4-hydroxyphenylpropionate], octadecyl-3-(3,5-di-tert-butyl-4-hydroxyphenyl)proprionate, 1,3,5-tris(3,5-di-tert-butyl-4-hydroxybenzyl)-2,4,6-trimethylbenzene, N,N'-bis(3,5-di-tert-butyl-4-hydroxyphenylpropionyl)hexamethylene-diamide or 1,3,5-tris[3,5-di-tert-butyl-4-hydroxybenzyl]isocyanurate, 2,4-di-t-butylphenyl-3,5-di-t-butyl-4-hydroxybenzoate or bis(1,2,2,6,6-pentamethylpiperidin-4-yl)-butyl(3,5-di-t-butyl-4-hydroxybenzyl)malonate), and the phenolic phosphite is tris[2,4-di-tert-butylphenyl] phosphite.

10. The composition according to claim 3, further comprising:
a sterically hindered amine light stabilizer different from the compound of the formula (I), and/or
an UV-absorber.

11. The composition according to claim 10, wherein the UV-absorber is present, and is selected from the group consisting of a 2-(2'-hydroxyphenyl)benzotriazole, a 2-hydroxybenzophenone, an oxamide and a 2-(2-hydroxyphenyl)-1,3,5-triazine.

12. The composition according to claim 3, further comprising a filler and/or a pigment.

13. An automotive interior or exterior trim material comprising the composition according to claim 3.

14. The automotive interior or exterior trim material according to claim 13, which is a facing material for a roof, seat or dashboard.

15. An agricultural article comprising the composition according to claim 3.

16. The agricultural article according to claim 15, which is a greenhouse cover.

17. A method for stabilizing an organic material against degradation induced by light, heat or oxidation, comprising incorporating into said organic material at least one compound of claim 1.

18. A method for preparing a compound of claim 1, comprising reacting a compound of formula (II)

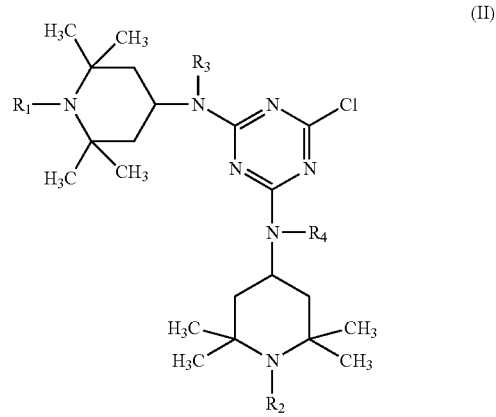

(II)

with pyrrolidine in an organic solvent, optionally in the presence of an organic or inorganic base.

* * * * *